United States Patent [19]

Maroney et al.

[11] Patent Number: 5,373,849
[45] Date of Patent: Dec. 20, 1994

[54] FORWARD VIEWING IMAGING CATHETER

[75] Inventors: John F. Maroney, Menlo Park; William N. Aldrich, Redwood City; William M. Belef, San Jose, all of Calif.

[73] Assignee: Cardiovascular Imaging Systems, Inc., Sunnyvale, Calif.

[21] Appl. No.: 6,224

[22] Filed: Jan. 19, 1993

[51] Int. Cl.⁵ .............................................. A61B 8/12
[52] U.S. Cl. .............................................. 128/662.06
[58] Field of Search ............... 128/4, 660.09, 660.1, 128/662.06

[56] References Cited

U.S. PATENT DOCUMENTS

| | | | |
|---|---|---|---|
| 3,955,561 | 5/1976 | Eggleton | 128/2.05 |
| 4,215,585 | 8/1980 | Kunii et al. | 73/633 |
| 4,375,818 | 3/1983 | Suwaki et al. | 128/4 |
| 4,399,703 | 8/1983 | Matzuk | 73/621 |
| 4,418,698 | 12/1983 | Dory | 128/660 |
| 4,424,813 | 1/1984 | Havlice et al. | 128/660.1 |
| 4,433,691 | 2/1984 | Bickman | 128/660 |
| 4,479,388 | 10/1984 | Matzuk | 73/634 |
| 4,515,017 | 5/1985 | McConaghy | 73/618 |
| 4,576,177 | 3/1986 | Webster, Jr. | 128/660 |
| 4,587,972 | 5/1986 | Morantte, Jr. | 128/660 |
| 4,785,819 | 11/1988 | Pearce | 128/660 |
| 4,794,931 | 1/1989 | Yock | 128/660 |
| 4,841,978 | 6/1989 | Eventoff et al. | 128/660 |
| 4,869,263 | 9/1989 | Segal et al. | 128/662.06 X |
| 4,936,307 | 6/1990 | Saito et al. | 128/662.06 |
| 5,000,185 | 3/1991 | Yock | 128/662 |
| 5,024,234 | 6/1991 | Leary et al. | 128/663 |
| 5,049,130 | 9/1991 | Powell | 604/96 |
| 5,090,414 | 2/1992 | Takano | 128/662.06 X |
| 5,161,537 | 11/1992 | Hashimoto et al. | 128/662.06 |
| 5,167,234 | 12/1992 | Watanabe et al. | 128/662.06 |
| 5,174,296 | 12/1992 | Watanabe et al. | 128/662.06 |

FOREIGN PATENT DOCUMENTS 0079284 5/1983 European Pat. Off. .
0129878 1/1985 European Pat. Off. .
0839368 8/1980 United Kingdom .

OTHER PUBLICATIONS

Bom, N. et al. Early and recent intraluminal ultrasound devices, *International Journal of Cardiac Imaging* 4: 79–88, 1989.
Feldman, C. L. "Coronary Artery Imaging System", PCT publ. No. WO92/19157 published 12 Nov. 1992.
Jongeling, J. M. et al "An Intra-Arterial Device", PCT Publ. No. WO/13253 published 15 Nov. 1990.
Bom, N. et al "Disposable Intra-Luminal UTS Instrument", EP 0423895 published 24 Apr. 1991.

*Primary Examiner*—Francis Jaworski
*Attorney, Agent, or Firm*—Townsend and Townsend Khourie and Crew

[57] ABSTRACT

An intraluminal imaging catheter system for viewing segments of vessels downstream of the catheter itself is provided. The catheter system incorporates an ultrasonic transducer pivotally mounted adjacent the catheter's distal end. A flexible drive means disposed within a flexible tubular member adapted for insertion into the vessel causes the transducer to pivot back and forth to scan a segment of the vessel. Optionally, the forward viewing catheter system of the present invention may be combined with a work element such as a biopsy tool or other device for use in conjunction with the imaging capability.

21 Claims, 5 Drawing Sheets

FORWARD VIEWING IMAGING CATHETER

BACKGROUND OF THE INVENTION

1. Field of the Invention

The present invention relates generally to a device and method for ultrasonic intraluminal imaging. More particularly, an intravascular catheter is provided for imaging a portion of a blood vessel in a plane extending axially from the tip of the catheter. The catheter system of the present invention may also include an additional diagnostic or interventional work element for use in conjunction with the imaging element.

2. Description of the Background Art

Arteriosclerosis, also known as atherosclerosis, is a common human ailment arising from the deposition of fatty-like substances, referred to as atheromas or plaque, on the walls of blood vessels. Such deposits occur in both peripheral blood vessels that feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma, atherectomy where a blade or cutting bit is used to sever and remove the atheroma, spark gap reduction in which an electrical spark burns through the plaque and laser angioplasty where laser energy is used to ablate at least a portion of the atheroma.

A major difficulty in using such devices is obtaining images and information on the region of the blood vessel to be treated. To overcome this difficulty, several techniques have been proposed for intraluminal imaging of vascular vessels. Catheters incorporating ultrasonic transducers for imaging are disclosed in U.S. Pat. Nos. 4,794,931; 5,000,185; 5,049,130; and 5,024,234. However, these catheters scan in a plane normal to the catheter axis. While such catheters are very useful for examining deposits adjacent to their distal tips, they are generally incapable of imaging the vessel downstream of the catheter.

Such downstream viewing would be useful in a variety of circumstances. For example, it would provide a visual determination of whether there is a channel through which a guide wire or catheter may be passed. Moreover, downstream viewing could provide information to help the physician to determine which type of intravascular device would be most suitable for reducing the stenosis. Finally, downstream viewing can be invaluable as an aid in directing and using interventional and diagnostic devices and avoiding accidental penetration of the vessel wall.

U.S. Pat. No. 4,576,177 to Webster describes a laser catheter having an ultrasonic transducer mounted at a fixed angle of inclination to the catheter tip. The transducer is not movable with respect to the catheter tip however, and is therefore only capable of imaging along a line fixed with respect to the catheter body.

U.S. Pat. No. 4,587,972 to Morantte discloses a catheter apparatus having an array of transducing elements. The elements are sequentially excited to obtain an image distal to the catheter. Such phased array devices are very complicated and therefore costly to fabricate. Their resolution and ability to steer the beam through a wide range of angles are limited by the number of elements provided.

It would be desirable to provide a catheter apparatus capable of imaging a blood vessel downstream of the catheter itself. It would be desirable if such a catheter were capable of scanning a region of the blood vessel in a plane located forward of the catheter. Such a catheter should be of relatively simple design to allow for compact construction and reliability of use. Additionally, it would be desirable to combine such a forward viewing catheter with an additional working element to provide the catheter system with a further diagnostic or interventional capability.

SUMMARY OF THE INVENTION

According to the present invention, a catheter system and device are provided that are capable of forward or "downstream" imaging of blood vessels and other body lumens and cavities within a patient. The catheter includes a flexible tubular member adapted for insertion into the vessel and an ultrasonic transducer disposed near the distal end of said flexible tubular member. A mechanism is provided for oscillating the transducer about a transverse axis (i.e., an axis normal to the longitudinal axis of the tubular member. The ultrasonic transducer is adapted to transmit and receive ultrasonic signals in a direction substantially forward of said distal extremity and is coupled to external video image processing circuitry which can thus present the desired forward view.

In a specific embodiment, the ultrasonic transducer is coupled to a flexible drive cable rotationally disposed in a lumen of the tubular member. The transducer is mechanically coupled to the drive cable by a mechanism that converts of rotation of the drive member into pivotal oscillation of the transducer with respect to the tubular member. This causes the transducer to scan a segment of the vessel in a plane aligned projecting forward of the catheter.

In another aspect of the invention, an imaging catheter system is combined with a biopsy device for sampling a deposit within the vessel. The biopsy device is disposed to permit simultaneous imaging and sampling of the deposit. Other work elements are possible as well. These additional work elements could include lasers, mechanical cutters, angioplasty balloons and the like, all of which are known in the art.

DETAILED DESCRIPTION OF THE SPECIFIC EMBODIMENTS

Figure 1:
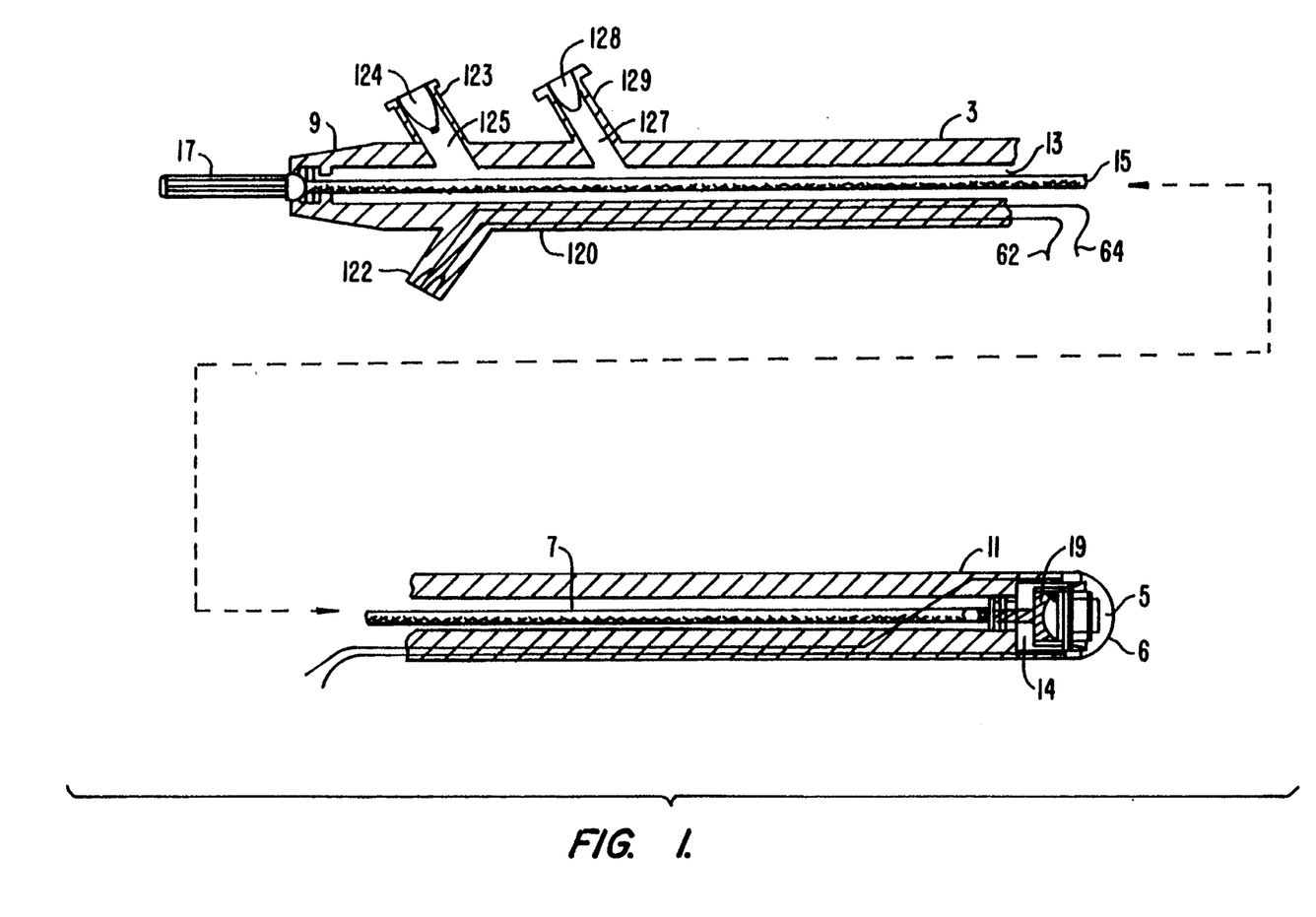
FIG. 1 is a side sectional view of a catheter having a forward viewing imaging capability according to the present invention.

A catheter system according to the present invention is illustrated in FIG. 1. The catheter system comprises a flexible tubular member 3, an ultrasonic transducer 5 and drive means 7. Tubular member 3 has a proximal end 9, a distal end 11 and a central lumen 13 connecting the two. Drive means 7 comprises a drive cable 15 rotatably disposed within central lumen 13 and a motor coupling 17 at the proximal end of the drive cable.

Ultrasonic transducer 5 is disposed within a distal housing 14 at distal end 11 of tubular member 3. The transducer is adapted for pivotal movement relative to the tubular member. The distal end of drive cable 15 is connected to the ultrasonic transducer by a coupling mechanism 19, which is adapted to convert rotation of the drive cable into pivotal oscillation of the ultrasonic transducer. Transducer 5 is shielded by a cover 6. The cover protects the transducer from interference by tissue within the patient and the patient from internal injury from contact with the rapidly oscillating transducer. Cover 6 is made of a acoustically transparent material to allow the transmission of the acoustic waves sent and received by transducer 5.

Figure 2:
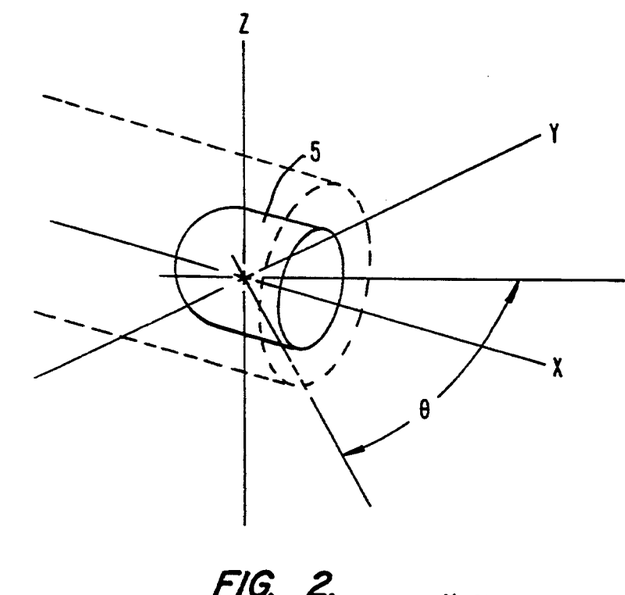
FIG. 2 is a diagrammatic view of a catheter tip in accordance with the present invention illustrating the planar scanning capability.

The pivotal motion of the ultrasonic transducer may be conveniently understood with reference to FIG. 2, which depicts the distal end 11 of tubular member 3, within which transducer 5 is mounted. Transducer 5 pivots within the tubular member about an axis Z and sweeps back and forth through an angle $\theta$ lying within a plane X-Y.

Figure 3:
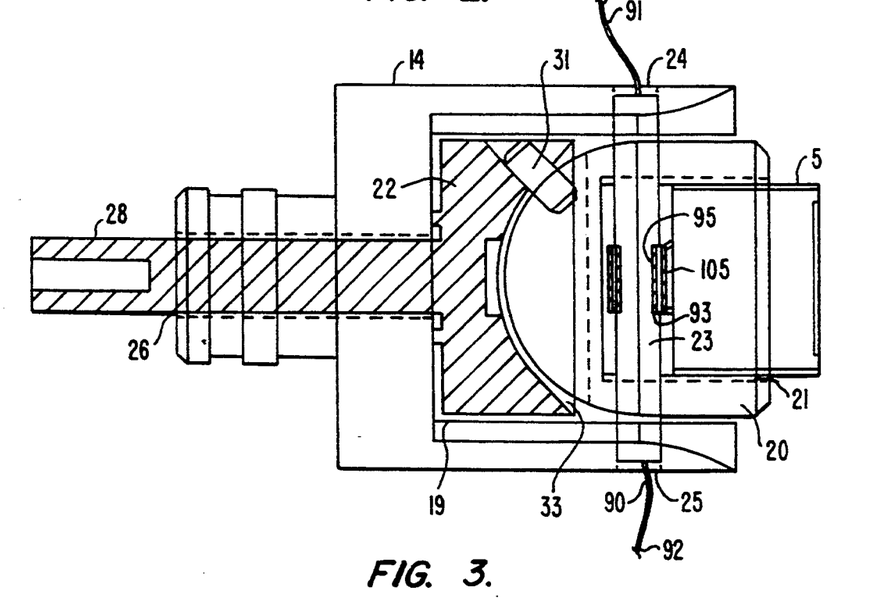
FIG. 3 is an enlarged side sectional view of a portion of FIG. 1 showing an assembled mechanism for converting rotation of a drive shaft into pivotal oscillation of an ultrasonic transducer.

Distal housing 14 and coupling mechanism 19 are shown in greater detail in FIG. 3. The distal housing holds the coupling mechanism. The coupling mechanism comprises three main parts: a transducer holder 20, which has a receptacle 21 in which the transducer is held; an actuator 22 for driving the transducer holder; and a stator 23, about which the transducer holder pivots.

Figure 4A:
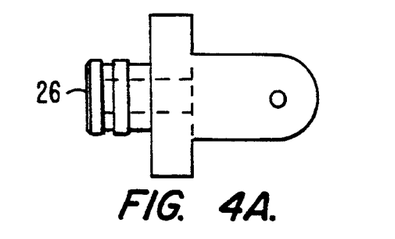
FIGS. 4–6 are multi-view orthogonal depictions of separate parts of the mechanism depicted in FIG. 3.
Figure 4B:
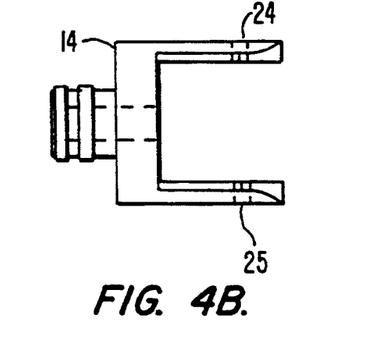
Figure 4C:
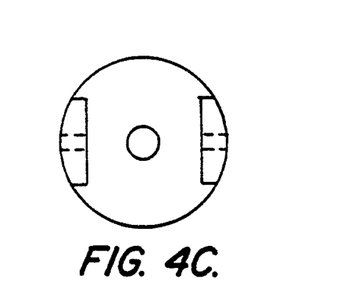

FIG. 4 is a three view orthogonal projection of distal housing 14. As can be seen therein, the distal housing has mounting holes 24 and 25 and a coaxial opening 26.

Figure 5A:
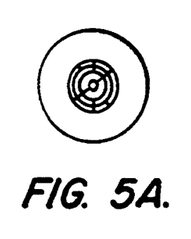
Figure 5B:
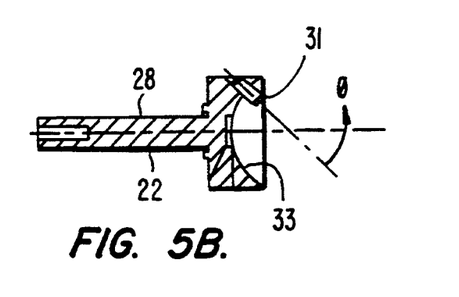

Actuator 22 is depicted in a two view orthogonal projection in FIG. 5. The actuator has a shaft 28 and an actuator pin 31 set into concave surface 33. The actuator pin is set at an angle $\phi$ to the center line of the actuator and the shaft. In a preferred embodiment of the invention, angle $\phi$ is about 45 degrees but the angle may vary without departing from the principles of the invention.

Figure 6A:
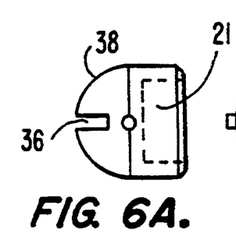
Figure 6B:
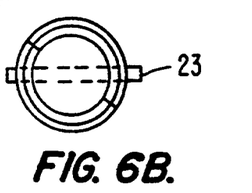

FIG. 6 is a two view projection of transducer holder 20 and stator 23 disposed therethrough. As mentioned previously, the transducer holder has a receptacle 21 for holding the transducer. The transducer holder also has a slot 36 cut into a rounded back surface 38. Slot 36 is adapted for cooperation with actuator pin 31 of actuator 22 and this will be described in more detail below.

Referring back to FIG. 3, the integration of the parts depicted in FIGS. 4–6 into the catheter system will now be described. Shaft 28 of actuator 22 is rotatably disposed through coaxial opening 26 of distal housing 14. The coaxial opening acts as a bearing to support the rotating shaft.

The ends of stator 23 are fixed (e.g., by a press fit) within mounting holes 24 and 25 of the distal housing. Transducer holder 20 is pivotally disposed about the stator. A pair of coils or windings disposed around the stator act as an inductive coupling 45 for electrical coupling of transducer 5 to an associated control means. The construction and function of inductive coupling 45 is discussed in detail below.

Actuator pin 31 is disposed for cooperation with slot 36. The width of slot 36 is slightly greater than the diameter of actuator pin 31 so that the pin may slide and rotate within the slot. The pin and slot are thus configured to convert rotation of actuator 22 into pivotal oscillation of transducer holder 20 about stator 23.

Figure 7:
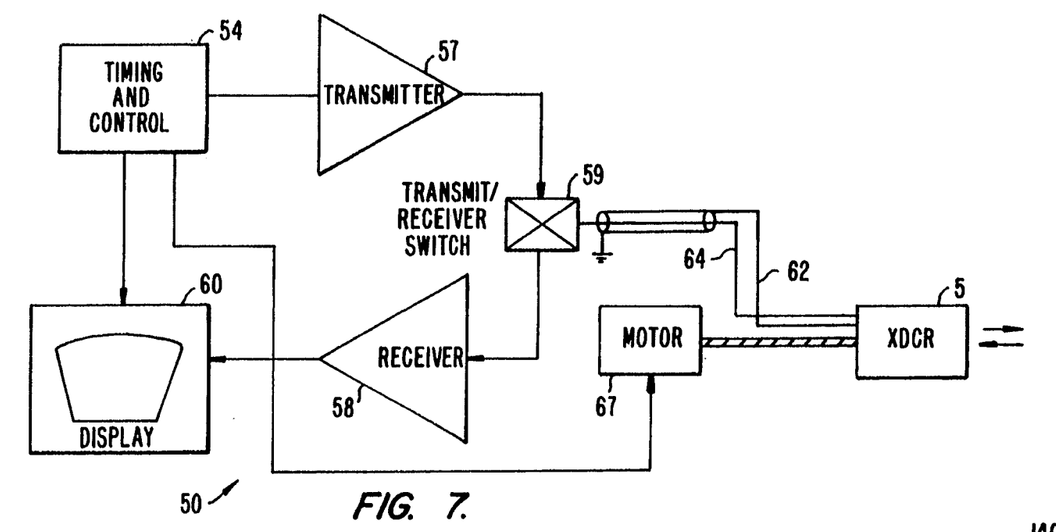
FIG. 7 is a schematic block diagram of a timing and control system suitable for use in the present invention.

System control circuitry 50 suitable for controlling the transducer is illustrated schematically in FIG. 7. The control circuitry, which can be formed of substantially conventional equipment, includes a timing and control means 54, a transmitter 57 and a receiver 58 with a transmit/receive switch 59, and a display unit 60, typically including a CRT tube for displaying an image from within the blood vessel.

In operation, timing and control means 54 sends pulses to transmitter 57. Transmitter 57 generates voltage for excitation of the transducer 5. The transducer generates ultrasonic energy waves which emanate forwardly into the blood vessel. Portions of the ultrasonic energy waves reflect from tissues within the vessel and are reflected back to the transducer. The transducer receives these reflected waves and converts them into electrical signals which are sent back to receiver 58 through conducting wires 62 and 64. The signals are amplified and processed by display unit 60, which converts the signals into a visual display of the structure of the vessel.

The transducer is switched between its send and receive modes by transmit/receive switch 59. Timing and control means 54 controls drive motor 67, which may be an open loop stepping motor or a closed loop servomotor. Motor 67 rotates drive cable 15, which, as discussed above, causes the transducer to scan back and forth through an arc within the blood vessel.

The scanned arc ($\theta$ in FIG. 2) will be 90 degrees in the embodiment depicted where actuator pin 31 is set at a 45 degree angle ($\phi$ in FIG. 5) to the axis of actuator shaft 28. Drive cable 15 is preferably rotated at a constant angular velocity. Eighteen hundred (1800) rpm is suitable rotation speed for the embodiment depicted. This translates to a transducer scan rate of 30 oscillations per second, a rate sufficient to provide good image detail with an acceptable image refresh rate. The transducer firing rate is coordinated with its pivotal movement by system controller 50. It will be understood that the actual transducer oscillation rate could be varied significantly within the scope of this invention.

Electrical signals are carried between the system controller and the transducer through conducting wires 62 and 64. The distal ends of these wires could be attached to the transducer in a conventional manner, e.g. by soldering. If this were done, sufficient slack would need to be left in the wires to allow for the pivotal oscillation of the transducer.

Direct connection of wires 62 and 64 to the transducer is problematic however, because of the high speed cyclic bending that directly connected wires would have to endure. As mentioned above, a typical transducer oscillation rate will be about 30 oscillations per second. Under sustained use, there is a very significant potential for fatigue failure either of the wires or the soldered connection between them and the transducer. A failure at either of these points would disable the system.

For these reasons, it is advantageous to eliminate the problem of flexing within wires 62 and 64 by using an indirect connection to electrically couple the wires to the transducer. An inductive coupling 45 adapted to this purpose is shown in place in FIG. 3.

Figure 8A:
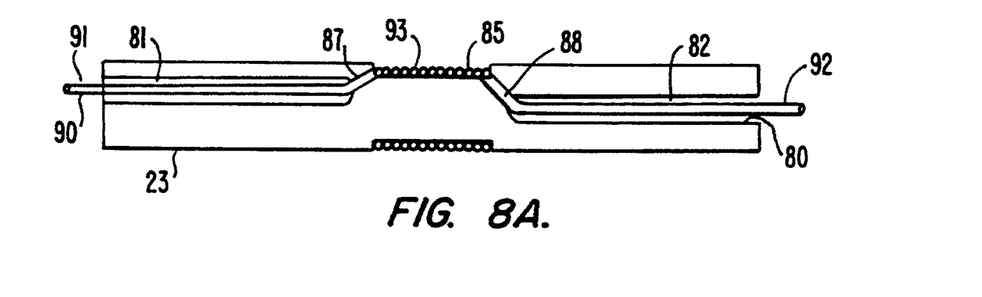
FIGS. 8A–8C illustrate the parts and assembly of an inductive coupling device for electrically connecting the connecting the ultrasonic transducer to the timing and control system.
Figure 8B:
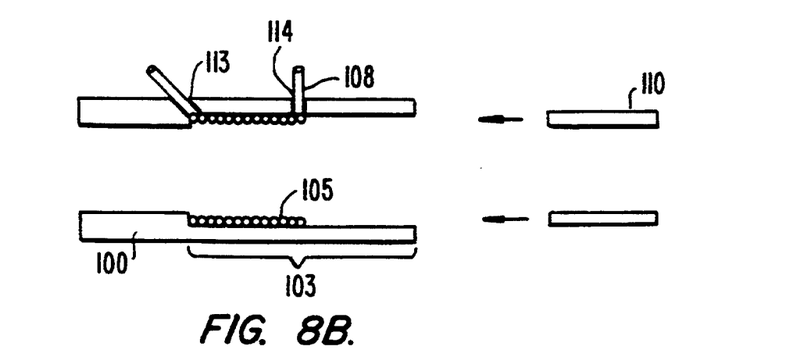
Figure 8C:
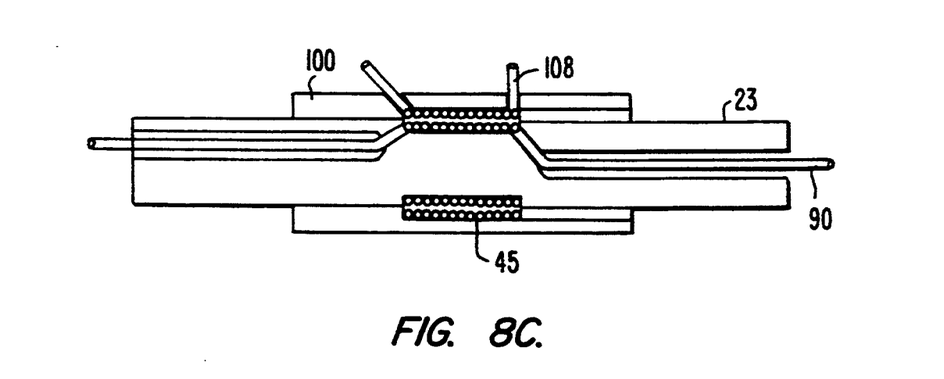
Figure 9:
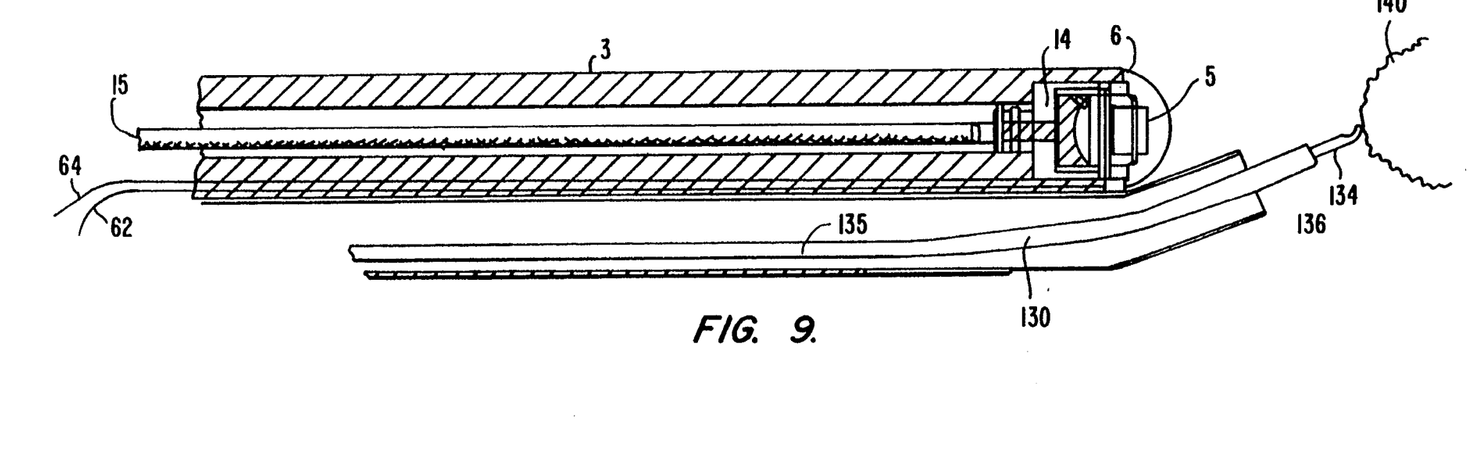
FIG. 9 is a side sectional view of a forward viewing imaging catheter according to the present invention combined with a biopsy tool for sampling a deposit within a blood vessel.

The details and construction of inductive coupling 45 are depicted in FIGS. 8A–8C. FIG. 8A depicts a stator assembly in detail. As can be seen therein, a wire channel 80, comprising channel segments 81 and 82, is bored partially through stator 23 from each end. A winding groove 85 is cut into the surface near the middle of the stator and stator holes 87 and 88 are drilled into the stator to connect winding groove 85 to channel segments 81 and 82.

Controller wire 90 is then fed through one channel segment, turned a number of times around the stator at winding groove 85, and fed out of the other channel segment. The turns of wire 90 within winding groove 85 form a stator winding 93 around stator 23. The number of turns in winding 93 may obviously vary but in one preferred embodiment there are thirteen turns.

A rotator assembly is depicted in detail in FIG. 8B. A rotator 100 has an inside diameter slightly larger than the outside diameter of stator 23 so that the rotator may be disposed to turn about the stator. Along a portion 103 of its length, rotator 100 has an even larger inside diameter to accommodate a winding 105 of transducer wire 108 and a retaining sleeve 110.

Rotator holes 113 and 114 are bored through the wall of rotator 100. Transducer wire 108 is fed through one of the holes, wound a number of times about the inside of the rotator to form a rotator winding 105, and finally fed back out through the second of the holes. Retaining sleeve 110 is then fitted within rotator 100 to hold rotator winding 105 in place. Rotator winding 105 will typically have the same number of turns as stator winding 93; in a preferred embodiment, thirteen.

As depicted in FIG. 8C, the rotator assembly is rotatably disposed about the stator assembly so that the windings are aligned with each other to form inductive coupling 45. An electrical current flowing within controller wire 90 will pass through stator winding 93 disposed within rotator winding 105. This will induce a corresponding electrical current within rotator winding 105 which will flow through transducer wire 108. The reverse will also be true—a current flowing through the transducer wire will induce a current within the controller wire.

Inductive coupling 45 is incorporated into the system as depicted in FIGS. 1 and 3. The two ends of stator 23 are press fit into mounting holes 24 and 25 of distal housing 14. The rotator is fixed within transducer holder 20, which pivots about the stator. The two ends 91 and 92 of controller wire 90 are routed back through tubular member 3, and serve as conducting wires 62 and 64. Transducer wire 108 is directly connected at each end to transducer 5.

Referring to FIG. 1, tubular member 3 of the catheter system has a three arm adaptor 120 at its proximal end. A first arm 122 of three arm adaptor 3 has conducting wires 62 and 64 routed through it and is adapted for connection with system controller 50 (FIG. 7).

A second arm 123 of the three arm adaptor has a fill port 124 and a fill channel 125 in communication with central lumen 13 of the tubular member. Before imaging, a fluid suitable for the transmission of ultrasonic signals will be injected into fill port 124. The fluid will fill the tubular member of the catheter system and flush air bubbles (which could interfere with imaging) out of the region of the transducer, along central lumen 13, and through a drain channel 127 and a drain port 128 of a third arm 129 of the three arm adaptor.

Electrical impulses will then be sent from the controller along conducting wires 62 and 64 and through stator winding 93. These impulses will induce corresponding impulses within rotator winding 105. The induced impulses will be carried to the transducer. The transducer will "fire" repeatedly, sending ultrasonic wave pulses into the blood vessel.

The ultrasonic waves will be reflected from structures within the blood vessels and returned to the transducer. The transducer will receive the reflected waves and convert them into electrical signals. The electrical signals will travel back through the inductive coupling and into conducting wires 62 and 64, which will then conduct the received signals back to the system controller for conversion by the display into visual images of the blood vessel. During imaging, the drive motor will continually rotate the drive cable causing the transducer to sweep back and forth to scan a plane within a region of the vessel lying forward of the catheter system.

Referring back to FIG. 2, it will be appreciated that by rotating the transducer about axis X as it pivots back and forth within plane X-Y, the transducer may be caused to scan a series of planes within the blood vessel and thereby to image a three-dimensional region of the blood vessel. In the simplest case, this may be done by simply rotating the entire catheter body within the patient's blood vessel. This will cause pivot axis Z of transducer 5 to rotate about axis X. The surgeon operating the system can simply form a mental image of a three dimensional region of the vessel as he rotates the catheter body through a series of imaging planes.

With further development, mechanical means for rotating pivot axis Z of the transducer about axis X could be devised. This mechanical rotation means could even be synchronized with the equipment for displaying the image, so that real time three dimensional images could be displayed directly by the imaging equipment.

A forward viewing imaging catheter system according to the present invention may be combined advantageously with other diagnostic or interventional work elements. FIG. 10 depicts a forward viewing imaging catheter in combination with a biopsy tool for sampling a deposit within the blood vessel. The deposit 129 depicted lies within the imaging plane of the catheter system. A biopsy tool 132 comprising a tool tip 134 and a tool shaft 135 is disposed within an additional tool lumen 136. The system depicted in FIG. 10 may greatly assist a physician in performing the biopsy procedure. The physician may conveniently view the deposit and the biopsy tip while the sample is being taken.

Other combinations are possible. For example, a rotating cutter, a balloon angioplasty device, a laser ablation device or some other device for treating a stenosis with the blood vessel could conveniently be carried by additional lumen 136. In such a system, the forward viewing capability would allow for simultaneous imaging and treatment of the region of interest within the vessel.

Although exemplary embodiments of the present invention have been described in some detail herein, the present examples and embodiments are to be considered as illustrative and not restrictive. The invention is not to be limited to the details given, but may be modified freely within the scope of the appended claims, including equivalent constructions.

What is claimed is:

1. A forward viewing imaging catheter system for imaging a blood vessel within a patient, the system comprising:
   a flexible tubular member adapted for insertion into the blood vessel, the tubular member having proximal and distal ends;
   an ultrasonic transducer located near the distal end of the tubular member and disposed to send and receive signals in a direction forward of the distal end; and
   means for oscillating the transducer about an axis perpendicular to a long axis of the tubular member, whereby oscillation of the transducer relative to the tubular member causes the transducer to scan an area forward of the catheter.

2. A catheter system for imaging a blood vessel within a patient, the device comprising:
   a flexible tubular member adapted for insertion into the blood vessel, the tubular member having proximal and distal ends;
   a flexible drive means disposed within the tubular member for rotational movement therein;
   an ultrasonic transducer pivotally coupled to the tubular member for transmitting and receiving ultrasonic signals in a direction substantially forward of the distal end of said tubular member, said ultrasonic transducer being coupled to said drive means;
   wherein rotational movement of said flexible drive means within the tubular member causes pivotal movement of the transducer to scan a segment of the vessel in a plane forward of the catheter.

3. A catheter system as recited in claim 2, further comprising a fill port and a drain port at the proximal end of the tubular member.

4. A catheter system as recited in claim 2, further comprising a motor coupling connected to the flexible drive means for connecting a motor to the drive means.

5. A catheter system as recited in claim 2, further comprising:
   a distal housing disposed near the distal end of the tubular member, said distal housing having a pair of opposing aligned holes;
   a transducer holder which receives the transducer and which is pivotally mounted on the stator;
   a stator set within said opposing aligned holes;
   wherein the transducer holder is mechanically coupled to said flexible drive means.

6. A catheter system as recited in claim 5, further comprising:
   an actuator coupled to the distal end of said flexible drive means, the actuator having a pin carried at an angle to the axis of rotation of the drive means;
   wherein said transducer holder is provided with a slot; and
   wherein said pin and slot cooperate to translate rotary motion of the drive means into pivotal movement of the transducer.

7. A catheter system as recited in claim 6, wherein the angle between the pin and the axis of rotation is between thirty and sixty degrees.

8. A catheter system as recited in claim 7, wherein the angle between the pin and the axis of rotation is substantially equal to forty-five degrees.

9. A catheter system as recited in claim 2, further comprising:
   a pair of wires disposed within the tubular member for transmitting electrical signals to and from the transducer means; and
   inductive coupling means electrically connecting the transducer to said pair of wires, said coupling means including a stator winding attached to the wire pair and a transducer winding attached to the transducer;
   wherein said stator and transducer windings are disposed concentric to one another.

10. A catheter system as recited in claim 2, further comprising a work element.

11. A catheter system as recited in claim 10, wherein the work element comprises a biopsy tool for sampling a deposit within the blood vessel.

12. A catheter system for obtaining an image of a blood vessel within a patient, the system comprising:
   a tubular member adapted to enter the blood vessel, the tubular member having proximal and distal ends;
   flexible drive means disposed within the tubular member for rotational movement within the tubular member;
   an ultrasonic transducer pivotally coupled to the tubular member near its distal end for transmitting and receiving ultrasonic signals in a direction substantially forward of the distal end of the catheter, the transducer being capable of receiving ultrasonic signals and translating the received ultrasonic signals into electrical receive signals, said ultrasonic transducer being mechanically coupled to the drive means for pivotal movement relative to the tubular member;
   transmitter means for producing an electrical transmit signal and supplying the transmit signal to the ultrasonic transducer to cause the transducer to generate ultrasonic signals;
   receiving means for receiving the electrical receive signals from the transducer; and
   a pair of wires disposed within the tubular member and electrically coupled to the transducer, said wires being connectable to the transmitter means and the receiving means.

13. A catheter system as recited in claim 12, further comprising means creating a visual display of a portion of the vessel being scanned by the ultrasonic transducer.

14. A catheter system as recited in claim 13, wherein the display means includes a cathode ray tube.

15. A catheter system as recited in claim 12, wherein said wires are electrically coupled to said ultrasonic transducer by an inductive coupling including a transducer winding attached to the transducer and a stator winding attached to the wires wherein said transducer winding and stator winding are disposed concentric to one another.

16. A catheter system as recited in claim 15, wherein the transducer winding and stator winding each comprise between five and twenty five coils.

17. A catheter system as recited in claim 15, wherein the stator winding lies within a winding groove disposed within a surface of a stator fixed near the distal end of the tubular member and about which the ultrasonic transducer pivots.

18. A catheter system as recited in claim 15, wherein the transducer winding is disposed within the transducer holder.

19. A method of intravascularly imaging a blood vessel using a catheter carrying an ultrasonic transducer near its distal extremity, the transducer for transmitting and receiving ultrasonic signals, the method comprising the steps of:

inserting the catheter into the blood vessel;

causing said transducer to emit ultrasonic signals;

receiving reflections of the emitted ultrasonic signals;

pivotally oscillating said transducer about a transverse axis relative to the catheter to scan a segment of the vessel substantially forward of the catheter; and processing the received signals to create an image of the scanned vessel segment along an axial plane relative to the catheter.

20. The method of claim 19, further comprising a step of rotating the transducer about an axis parallel to the long axis of the catheter body, whereby the transducer is caused to scan a series of planes comprising a three-dimensional region of the interior of the vessel.

21. The method of claim 19, further comprising a step of using a biopsy tool to sample an obstruction lying within the scanned segment of the vessel.

* * * * *